US009718745B2

(12) United States Patent
Yang et al.

(10) Patent No.: US 9,718,745 B2
(45) Date of Patent: Aug. 1, 2017

(54) PREMIXER, RADIALLY FIXED BED REACTOR, REACTION SYSTEM FOR OXIDATIVE DEHYDROGENATION (71) Applicants: CHINA PETROLEUM & CHEMICAL CORPORATION, Beijing (CN); Shanghai Research Institute of Petrochemical Technology, SINOPEC, Shanghai (CN)

(72) Inventors: Weimin Yang, Shanghai (CN); Wenjie Liu, Shanghai (CN); Yunqun Huang, Shanghai (CN); Yi Guo, Shanghai (CN); Depan Shi, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 544 days.

(21) Appl. No.: 14/164,549

(22) Filed: Jan. 27, 2014

(65) Prior Publication Data
US 2014/0221719 A1 Aug. 7, 2014

(30) Foreign Application Priority Data

Jan. 30, 2013 (CN) .......................... 2013 1 0034156
Jan. 30, 2013 (CN) .......................... 2013 1 0034285

(51) Int. Cl.
*B01J 8/04* (2006.01)
*C07C 5/48* (2006.01)
(Continued)

(52) U.S. Cl.
CPC .............. *C07C 5/48* (2013.01); *B01J 8/0214* (2013.01); *B01J 8/0278* (2013.01); *B01J 8/04* (2013.01);
(Continued)

(58) Field of Classification Search
USPC ........................................ 422/218, 636, 637
See application file for complete search history.

(56) References Cited

U.S. PATENT DOCUMENTS 2,325,905 A * 8/1943 Caulfield ................. F01N 1/08
181/268
2,634,194 A * 4/1953 Nebeck ................. B01J 8/0085
196/133
(Continued)

FOREIGN PATENT DOCUMENTS

CN          1468651 A      1/2004
CN          1751781 A      3/2006
(Continued)

*Primary Examiner* — Jennifer A Leung
(74) *Attorney, Agent, or Firm* — Novick, Kim & Lee, PLLC; Allen Xue (57) ABSTRACT The present disclosure provides a premixer for at least two gases, comprising: a tubular body having a closed end and an opposite, open end; a first flow passage for receiving a first gas, the first flow passage axially extending through the closed end into the tubular body in a sealable manner; a conical tube arranged in the tubular body, wherein a small end of the conical tube communicates with the first flow passage, and a large end of the conical tube extends toward the open end with an edge thereof being fixed to an inner wall of the tubular body, thereby defining a sealed distribution chamber between the tubular body and the conical tube; and a second flow passage arranged on a side portion of the tubular body for receiving a second gas, wherein the second flow passage communicates with the distribution chamber, so that the second gas can be introduced into said conical (Continued)

tube via the distribution chamber in a substantially radial manner. The present disclosure further relates to a radially fixed bed reactor comprising the premixer, a reaction system of oxidative dehydrogenation of butene comprising the racially fixed bed reactor, and a corresponding process.

24 Claims, 5 Drawing Sheets

(51) Int. Cl.
 *C07C 11/167* (2006.01)
 *B01J 8/02* (2006.01)
(52) U.S. Cl.
 CPC ...... *B01J 8/0457* (2013.01); *B01J 2208/0092* (2013.01); *B01J 2208/00176* (2013.01); *B01J 2208/00477* (2013.01); *B01J 2208/00849* (2013.01); *B01J 2208/00902* (2013.01); *B01J 2208/00929* (2013.01); *B01J 2208/00938* (2013.01); *B01J 2219/0004* (2013.01); *B01J 2219/00038* (2013.01); *C07C 2523/02* (2013.01); *C07C 2523/06* (2013.01); *C07C 2523/26* (2013.01); *C07C 2523/72* (2013.01); *C07C 2523/745* (2013.01); *C07C 2523/75* (2013.01); *C07C 2523/755* (2013.01); *C07C 2527/185* (2013.01); *C07C 2527/188* (2013.01)

(56) References Cited

U.S. PATENT DOCUMENTS

| | | | | |
|---|---|---|---|---|
| 3,479,146 A | * | 11/1969 | Hochman | B01J 8/0278 208/146 |
| 3,646,239 A | * | 2/1972 | Hutson, Jr. et al. | C02F 3/344 210/611 |
| 3,751,511 A | | 8/1973 | Calihan et al. | |
| 3,758,279 A | * | 9/1973 | Whitesides | B01J 8/0403 210/282 |
| 4,169,879 A | * | 10/1979 | Descoins | B01J 8/0214 422/218 |
| 4,374,094 A | | 2/1983 | Farnham | |
| 2005/0171311 A1 | | 8/2005 | Schindler et al. | |
| 2007/0196252 A1 | | 8/2007 | Pawlak et al. | |
| 2008/0107575 A1 | | 5/2008 | Vetter et al. | |
| 2013/0221123 A1 | * | 8/2013 | Oshinowo | B01J 19/0053 239/1 |

FOREIGN PATENT DOCUMENTS

| | | |
|---|---|---|
| CN | 101367702 A | 2/2009 |
| CN | 101367702 B | 6/2012 |
| CN | 102516008 A | 6/2012 |
| CN | 102658042 A | 9/2012 |
| CN | 202527113 U | 11/2012 |
| EP | 0619457 A1 | 10/1994 |
| EP | 2256101 A2 | 12/2010 |

\* cited by examiner

PREMIXER, RADIALLY FIXED BED REACTOR, REACTION SYSTEM FOR OXIDATIVE DEHYDROGENATION

TECHNICAL FIELD

The present disclosure relates to a premixer for gases, a radially fixed bed reactor comprising said premixer, a reaction system for oxidative dehydrogenation of butene comprising said radially fixed bed reactor, and a process for preparing butadiene using said system.

TECHNICAL BACKGROUND

As an important monomer in synthetic rubber and synthetic resin, butadiene is mainly used for synthesizing butadiene rubber, styrene butadiene rubber, nitrile rubber, ABS resin, etc. Besides, butadiene also serves as a feed stock in the preparation of coatings and in some organic chemical reactions.

Oxidative dehydrogenation of butene is currently a competitive process in producing butadiene, wherein butadiene and water of stable structures are obtained by the combination of oxygen and hydrogen in butene molecules in the presence of steam. Oxidative dehydrogenation of butene is substantially irreversible, with the main reaction equation as follows:

$$2C_4H_8 + O_2 \rightarrow 2C_4H_6 + 2H_2O + 127.9 \text{ kJ/mol}$$

And the following reaction equations reflect the side reactions in oxidative dehydrogenation of butene:

$$C_4H_8 + 4O_2 \rightarrow 4CO + 4H_2O$$

$$C_4H_8 + 6O_2 \rightarrow 4CO_2 + 4H_2O$$

The main factors that would influence oxidative dehydrogenation of butene involve reaction temperatures, reaction pressures, the ratio of water to butene, the ratio of oxygen to butene, etc. In the reaction process, it is necessary to introduce a great deal of steam to facilitate protection of catalysts and control of the reaction temperature. Generally, the molar ratio of steam to the feed stock of butene reaches 8:1 to 16:1 or even higher. As to oxygen, since it participates in both the main reaction and side reactions, the adding amount thereof not only influences the conversion of butene, but also determines the degree to which the main and side reactions take place. Where the molar ration of oxygen to butene is too high, there would be more oxygen compounds and complete oxidation of butene as well, while too low a ratio of oxygen to butene would severely lower the conversion of butene. Furthermore, the adding amount of oxygen also concerns safety of the production. For example, the raw material formulation can by no means fall within the explosion limit. Moreover, inhomogeneous distribution of oxygen can also raise safety problems. Hence, feed stocks such as butene, air, and steam must be homogenously mixed after entering the oxidative dehydrogenation reactor. Otherwise, different amounts of steam at different catalyst bed layers in the reactor would cause carbon deposit rather fast. As can be concluded, the mixing homogeneity of the feed stocks is of essential importance to use of the overall oxidative dehydrogenation technology.

An axially fixed bed is now widely adopted in the preparation of butadiene by oxidative dehydrogenation of butene, as being recited, for example, in CN101367702. Although the axially fixed bed is of simple structures, the height of a catalyst bed layer thereof is restricted in order to satisfy the requirement of lowering the pressure drop. Furthermore, where an axially fixed bed is used, the production scale of the apparatus for oxidative dehydrogenation of butene would usually fall within the range from 5,000 to 15,000 tons per year. Nevertheless, as butadiene is increasingly required and the oxidative dehydrogenation technology is progressed, the production scale of an apparatus for preparing butadiene reaches more than 100,000 tons per year. Hence, four or even more reaction lines, such as 8 axial reactors divided into 4 groups, are required in the apparatus comprising such axially fixed bed reactors, which results in complex operations, and large investment and floor areas.

CN2626604Y discloses a radial reactor with a fluid substantially distributed in a homogeneous manner. However, this radial reactor fails to achieve homogeneous mixing of fluids entering a passage, and is of complicated structures and large pressure drop. CN102675027A, for example, discloses a process for preparing butadiene by oxidative dehydrogenation of butene using a radially fixed bed, wherein the apparatus thereof is also of complicated structures and large pressure drop, and is silent on a very important issue, i.e., homogeneous mixing of feed stock gasses, whereby the industrial use of oxidative dehydrogenation of butene is significantly limited.

SUMMARY OF THE INVENTION

The present disclosure aims to provide a premixer for gases, which can in particular be used for oxidative dehydrogenation of butene, so as to achieve fast and homogeneous mixing of feed stocks of butene, steam, and air, and to avoid problems such as carbon deposits, short catalyst regeneration cycle, etc. The present disclosure further relates to a radially fixed bed reactor comprising said premixer for oxidative dehydrogenation of butene, and a reaction system comprising said radially fixed bed reactor for oxidative dehydrogenation of butene.

According to a first aspect of the present disclosure, it provides a premixer for at least two gases, comprising: a tubular body having a closed end and an opposite, open end; a first flow passage for receiving a first gas, the first flow passage axially extending through the closed end into the tubular body in a sealable manner; a conical tube arranged in the tubular body, wherein a small end of the conical tube communicates with the first flow passage, and a large end of the conical tube extends toward the open end with an edge thereof being fixed to an inner wall of the tubular body, thereby defining a sealed distribution chamber between the tubular body and the conical tube; and a second flow passage arranged on a side portion of the tubular body for receiving a second gas, wherein the second flow passage communicates with the distribution chamber, so that the second gas can be introduced into said conical tube via the distribution chamber in a substantially radial manner.

In one embodiment, the first flow passage is in the form of a tubular passage, which extends into the conical tube by sealably passing through the small end thereof.

Preferably, an end of the first flow passage extending into the conical tube comprises a perforated distribution plate, which is in the form of a hemisphere, a cone or a plate, the perforations therein having a diameter in the range from 5 to 100 mm, preferably from 20 to 60 mm.

In one embodiment, a half cone angle of the conical tube is in the range from 5 to 20°, preferably from 8 to 16°.

In one embodiment, a nozzle is provided in a side portion of the conical tube adjacent to the small end thereof for introducing the second gas into the conical tube, the nozzle being preferably configured as a guiding cone. Preferably, the nozzle comprises a plurality of groups of guiding cones respectively arranged in the side portion of the conical tube at different heights, each group comprising a plurality of guiding cones circumferentially arranged in a homogeneous manner, wherein it is preferred that corresponding guiding cones in every two adjacent groups are staggered from each other in a circumferential direction.

In one embodiment, the premixer communicates with a reactor for oxidative dehydrogenation of butene via the open end thereof, wherein the first gas is a mixture of steam and an oxygen-containing gas, and the second gas is butene.

According to a second aspect of the present disclosure, it provides a radially fixed bed reactor for oxidative dehydrogenation of butene, comprising: a premixer according to the first aspect of the present disclosure; a cylindrical housing with a top end communicating with the open end of the tubular body of the premixer; a catalyst bed assembly arranged in the housing, the catalyst bed assembly including a plurality of sector tube distributors which are provided on an inner wall of the housing, a porous wall tube which is provided in the center of the housing and extends outside from the housing, and a catalyst bed disposed between the sector tube distributors and the porous wall tube, wherein a sealing member is arranged at an upper end of the catalyst bed, which allows mixed gases from the premixer to be introduced into the sector tube distributors and then be discharged from the housing after passing through the catalyst bed and porous wall tube; and a gas distributor which connects to the open end of the tubular body of the premixer and extends into the housing, a lower end of the gas distributor being provided with a cone-shaped baffle tapered toward the tubular body, whereby premixed gases from the premixer enter the housing via a lateral annular gap formed between the cone-shaped baffle and the housing.

In one embodiment, the gas distributor further comprises a plurality of webs circumferentially arranged in a homogeneous manner for connecting the cone-shaped baffle to the open end of the tubular body of the premixer. A cone angle of the cone-shaped baffle ranges from 90 to 135°, preferably from 120 to 135°. Furthermore, the lateral annular gap is arranged in such a size that the mixed gasses flowing therethrough maintains an average speed in the range from 10 to 40 m/s, preferably from 20 to 35 m/s.

In one embodiment, the sector tube distributors comprise at least 6 sector tubes which are circumferentially distributed in a homogeneous manner and substantially constitute a whole circumference, an inner side surface and a top portion of the sector tube both being provided with distribution orifices. The porosity of the distribution orifices ranges from 10% to 50%, preferably from 20% to 40%.

In one embodiment, the porous wall tube comprises a porous cylinder positioned in a center thereof, a perforated plate abutting against the porous cylinder, and a screen or grill at an outer side thereof, wherein the screen and the perforated plate are connected to each other via support ribs, or the grill abuts against the perforated plate.

According to a third aspect of the present disclosure, it provides a system for preparing butadiene by oxidative dehydrogenation of butene, comprising a first stage reactor and a second stage reactor in series connection with each other, wherein the first stage reactor is in the form of an axially fixed bed reactor, while the second stage reactor is a radially fixed bed reactor according to the second aspect of the present disclosure; alternately, the first stage reactor is a radially fixed bed reactor according to the second aspect of the present disclosure, while the second stage reactor is in the form of an axially fixed bed reactor.

Preferably, the axially fixed bed reactor comprises at least two axially fixed bed reactors connected to each other in parallel.

According to a fourth aspect of the present disclosure, it provides a process for preparing butadiene by a system as set forth in the third aspect of the present disclosure, comprising the following steps: a) feeding steam into the first stage reactor, and feeding a butene-containing gas and an oxygen-containing gas into both the first stage reactor and the second stage reactor, wherein the molar ratio of butene to oxygen to steam fed into the first stage reactor ranges from 1:(0.4-1.5):(2-20); b) allowing materials output from the first stage reactor to mix with the butene-containing gas and oxygen-containing gas before entering the second stage reactor, wherein the molar ratio of butene to oxygen to steam fed into the second stage reactor ranges from 1:(0.4-1.5):(2-20); and c) allowing materials output from the second stage reactor to enter a downstream separation stage for recovering butadiene; wherein the reaction temperatures in the first and second stage reactors are in the range from 300 to 600° C., and the reaction pressures thereof are in the range from 0.0 to 2.0 MPaG.

In one embodiment, said butene-containing gas comprises at least one selected from the group consisting of 1-butene, cis-2-butene, and trans-2-butene.

In one embodiment, the molar ratio of butene to oxygen to steam entering each stage is in the range from 1:(0.45-0.9):(6-16), preferably from 1:(0.5-0.8):(6-12), and more preferably from 1:(0.5-0.7):(6-10). The gaseous hourly space velocity of butene entering each stage ranges from 200 to 450 $h^{-1}$.

In one embodiment, the reaction temperature in each stage ranges from 310 to 480° C., preferably from 310 to 380° C., and the reaction pressure in each stage ranges from 0.05 to 0.5 MPaG.

DETAILED DESCRIPTION OF EMBODIMENTS

The present disclosure will be explained in detail with reference to the appended drawings.

Figure 1:
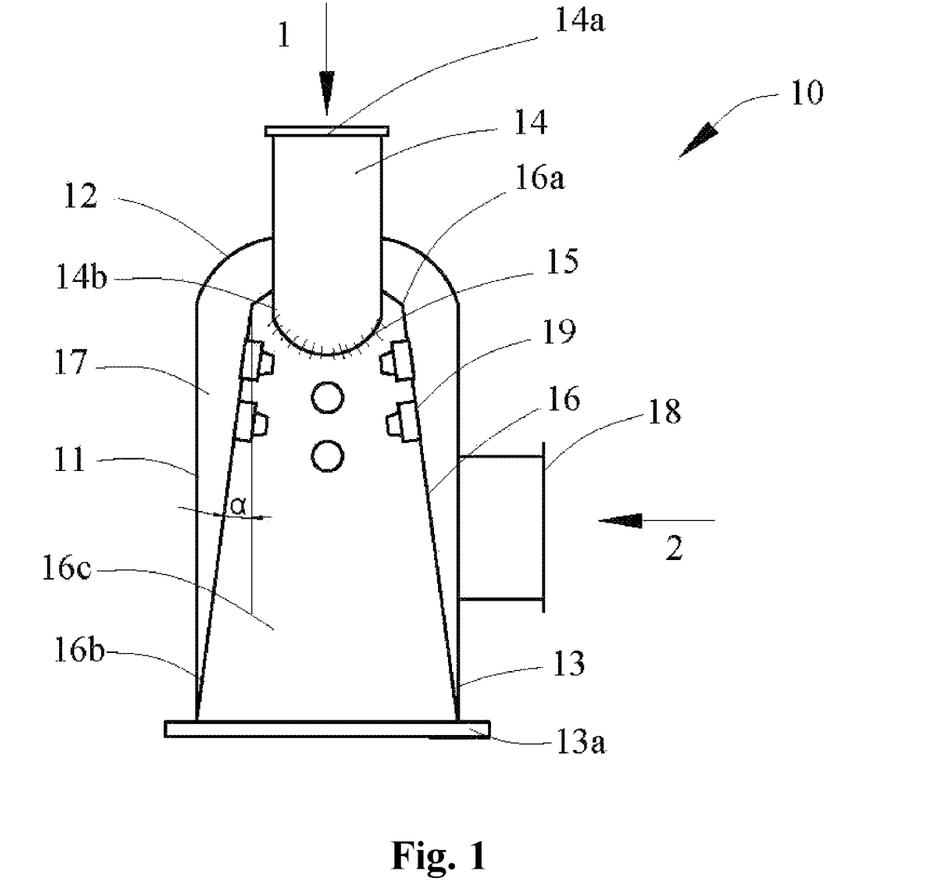
FIG. 1 schematically shows the structure of a premixer according to the present disclosure.

FIG. 1 schematically shows the structure of a premixer for at least two gases according to the present disclosure. As indicated in the Figure, a premixer 10 according to the present disclosure comprises a tubular body 11 which has a closed end 12 and an opposite, open end 13.

A first end 14a of a first flow passage 14 in the form of a tube connects to a supply of a first gas 1 which is not shown in FIG. 1, while a second end 14b extends through the closed end 12 of the tubular body 11 into the tubular body 11 along an axial direction thereof in a sealable manner. Hence, the first flow passage 14 can introduce the first gas 1 into the tubular body 11.

In the embodiment as illustrated in FIG. 1, the second end 14b of the first flow passage 14 comprises a perforated distribution plate 15, which is configured, for example, in the form of a hemisphere, a cone or a plate. The perforated distribution plate 15 is provided with a plurality of perforations for introducing the first gas 1 into the tubular body 11, wherein the perforations each have a diameter that can be selected in the range from 5 to 100 mm, preferably from 20 to 60 mm. However, it can be easily understood that in one embodiment not shown, the second end 14b of the first flow passage 14 can be provided with no distribution plates 15. That is, the second end 14b can be configured as being open so as to introduce the first gas 1 into the tubular body 11 directly.

According to the present disclosure, the tubular body 11 is further provided with a conical tube 16 therein. The conical tube 16 has a closed, small end 16a, wherein the second end 14b of the first flow passage 14 extends through the small end 16a of the comical tube 16 into the conical tube 16 along an axial direction in a sealable manner. In this way, the first flow passage 14 can introduce the first gas 1 into a mixing chamber 16c of the conical tube 16. Furthermore, a large end 16b (which is an open end) of the conical tube 16 extends toward the open end 13 of the tubular body 11, and is fixed on an inner wall of the tubular body 11 at an edge 13a thereof. Therefore, a sealed distribution chamber 17 is defined between the tubular body 11 and the conical tube 16.

A side portion of the tubular body 11 is further provided with a second flow passage 18 for receiving a second gas 2. The second flow passage 18 is, for example, also in the form of a tube which communicates with the distribution chamber 17, so as to allow the second gas 2 to be introduced into the distribution chamber 17, and further into the mixing chamber 16c of the conical tube 16 in a substantially radial manner via the distribution chamber 17.

In the embodiment as shown in FIG. 1, a plurality of nozzles 19 are mounted in a side wall of the conical tube 16 adjacent to the small end 16a for introducing the second gas 2 into the conical tube 16 from the distribution chamber 17 along a substantially radial direction. The nozzles 19, which can be divided into one to eight groups with altogether 2 to 20 of them, are preferably configured to be in the form of a guiding cone, with each group being arranged at different axial positions, i.e., different heights as shown in FIG. 1. In some preferred embodiments, the nozzles 19 can be divided into 2 to 4 groups, each group having 2 to 3 nozzles. It is easily understood that the number of the above nozzles can be readily selected according to actual conditions.

Therefore, according to the present disclosure, the first gas 1 is introduced into the mixing chamber 16c of the conical tube 16 via the first flow passage 14 in a substantially axial manner. Meanwhile, the second gas 2 enters the distribution chamber 17 via the second flow passage 18, and is introduced in a substantially radial manner to the mixing chamber 16c of the conical tube 16 therefrom. Thus, the first gas 1 and the second gas 2 mix with each other in the mixing chamber 16c before being output from the open end 13 of the tubular body 11, so as to be used in a suitable reactor arranged downstream (not shown). Since the first gas 1 and the second gas 2 enter the mixing chamber 16c in a substantially axial and radial manner respectively, effective collision between these two gases can be achieved, so as to facilitate fast and homogeneous mixing.

The premixer 10 according to the present disclosure can especially be used in a system for preparing butadiene by oxidative dehydrogenation of butene. Under this circumstance, the first gas 1 is a mixture of steam and an oxygen-containing gas (e.g. air), while the second gas 2 is butene (or a butene-containing gas). In one exemplary embodiment, the molar ratio of butene to oxygen to steam can be selected as within the range from 1:(0.4-1.5):(2-20), preferably from 1:(0.5-1.2):(4-15), and more preferably from 1:(0.45-0.9):(5-12).

Hence, in the premixer 10 used in the preparation of butadiene by oxidative dehydrogenation of butene, a preferably overheated mixture of steam and air is introduced via the first end 14a of the first flow passage 14 in the form of a tube, from a top end of the tubular body 11 in the form of a straight tube, and enter the mixing chamber 16c of the conical tube 16 directly, or via the perforated distribution plate 15. At the same time, butene enters the distribution chamber 17 via the second flow passage 18 from the side portion of the tubular body 11, then enters the mixing chamber 16c via the nozzles 19 arranged on the conical tube 16, and therefore mixes with the overheated mixture of steam and air in the mixing chamber 16c. The pressure drop of butene entering the mixing chamber 16c can be lowered by the nozzles 19. Furthermore, the density of butene is three times as high as that of the mixture of steam and air, whereby a high-density butene stream would collide with the mixture of steam and air in high momentum via the nozzles 19, and thereby achieves fast and homogeneous mixing with one another with a low pressure drop. A mixed stream is conveyed into a downstream reactor in the reaction system, for the oxidative dehydrogenation of butene.

In one embodiment, a half cone angle α of the conical tube 16 is in the range from 5 to 20°, preferably from 8 to 16°, the selection of which can facilitate homogeneous mixing.

In one embodiment not shown, the circumferential positions of the nozzles in every two adjacent groups are different from each other, i.e., each nozzle is staggered from the corresponding nozzle in an adjacent group in a circumferential direction. In this way, the second gas can be introduced into the conical tube 16 in a more homogeneous manner, which ensures homogeneous mixing between the second and the first gases.

In the following, a radially fixed bed reactor 50 for oxidative dehydrogenation of butene according to the present disclosure will be explained with reference to FIGS. 2 and 3. As indicated in the Figures, the radially fixed bed reactor 50 comprises a cylindrical housing 20, which is provided with an upper head 21 and a lower head 22 respectively at an upper end and a lower end thereof. The premixer 10 according to the present application extends through the upper head 21 into the housing 20 in a sealable manner, for supplying the mixed stream of the first gas 1 and the second gas 2 into the housing 20.

According to the present disclosure, a catalyst bed assembly 40 is arranged inside the housing 20 of the radially fixed bed reactor 50. The catalyst bed assembly 40 includes a plurality of sector tube distributors 41 arranged in an inner wall of the housing 20. These sector tube distributors 41 are adjacently arranged along a circumferential direction, and form a circumferentially integral structure. A plurality of orifices is arranged both in a top wall and an inner side wall of each of the sector tube distributors 41.

The catalyst bed assembly 40 further comprises a porous wall tube 45, which is disposed at the center of the housing 20, and extends through the lower head 22 in a sealable manner to the outside of the housing 20. A side wall of the porous wall tube 45 is provided with a plurality of orifices (not shown). Besides, the catalyst bed assembly 40 further comprises a catalyst bed 42 disposed between the sector tube distributors 41 and the porous wall tube 45. An upper end of the catalyst bed 42 is arranged with a sealing member 47, which, for example comprises a ceramic ball and a cover plate.

In one embodiment, the catalyst bed 42 contains an iron-based composite oxide catalyst which has a spinel structure for the preparation of butadiene by oxidative dehydrogenation of butene, the formula of the catalyst based on the chemical composition thereof being $Fe_2O_3 \cdot MgO \cdot ZnO \cdot P_2O_5 \cdot M_xO_y$, wherein M is at least one selected from the fourth period in the Element Periodical Table, i.e., the elements of Sc, Ti, V, Cr, Fe, Mn, Co, Ni, Cu, and Zn.

Figure 2:
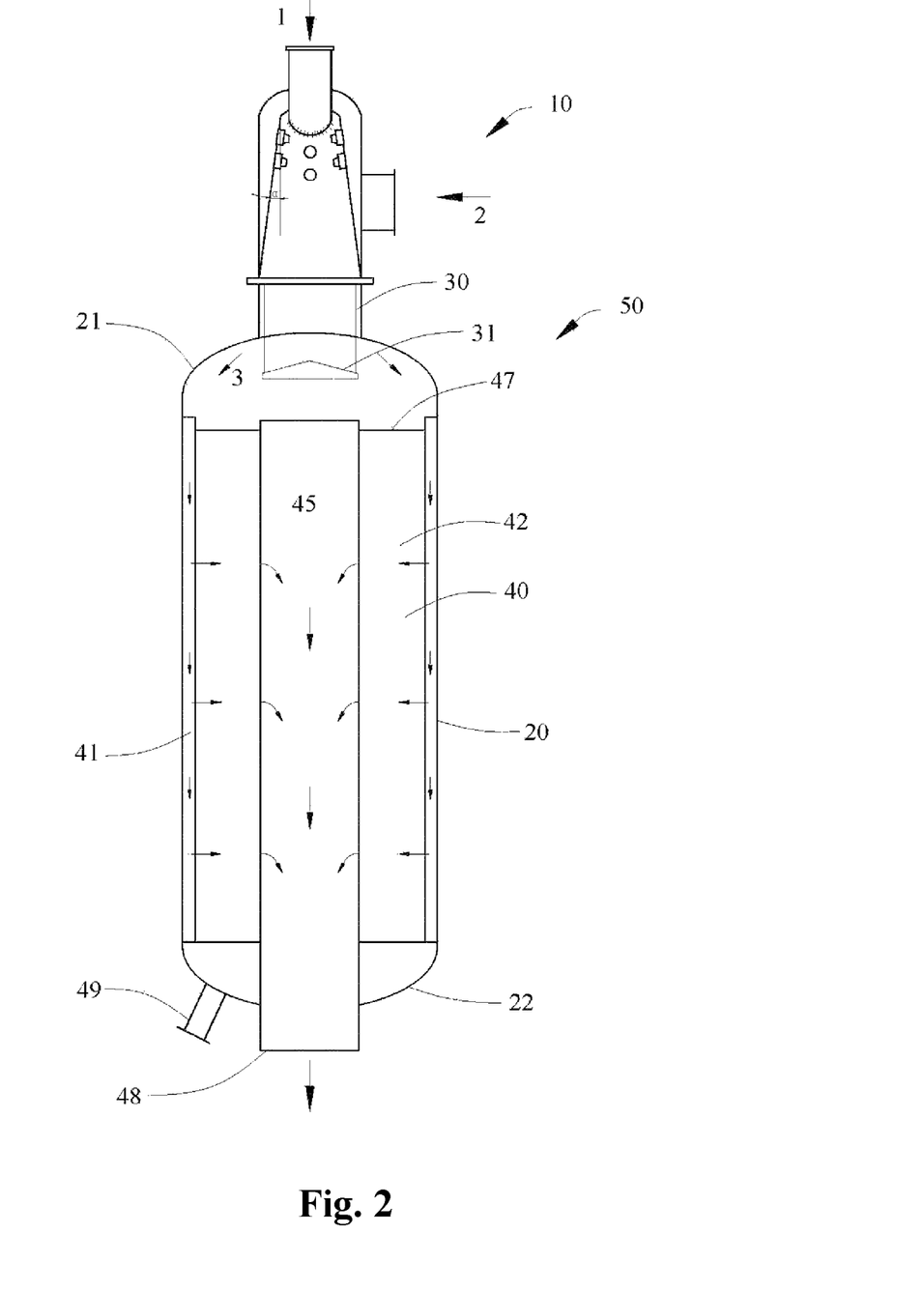
FIG. 2 schematically shows the structure of a radially fixed bed reactor according to the present disclosure.

Hence, as illustrated by the thin arrows in FIG. 2, a mixed stream 3 from the premixer 10 would enter an inner passage of the sector tube distributors 41 via the orifices in the top wall of the sector tube distributors 41, and then enter the catalyst bed 42 via the orifices on the inner side wall thereof. Afterwards, the mixed stream enters the porous wall tube 45 via the orifices arranged on the side wall thereof, and flows downward out of the housing 20 via a discharging outlet 48. The spent catalyst is dischargeable from a port 49.

In the radially fixed bed reactor 50, when the mixed stream 3 from the premixer enters the housing 20 from an inlet at a top portion thereof in a jet, there will be a sudden expansion of flow area, thereby leading to an extremely inhomogeneous distribution of gas streams in the sector tube distributors 41. As a result, a portion of the catalyst is overloaded and deactivated too early, thus significantly increasing carbon deposits of the catalyst, and occurrence probability of side reactions, which would affect the product quality. Meanwhile, the rest catalyst is almost ineffective.

To solve the above technical problems, according to the present disclosure, the open end of the tubular body 11 of the premixer 10 is provided with a gas distributor 30, a lower end of which is arranged with a cone-shaped baffle 31 tapered toward the tubular body 11. The cone-shaped baffle 31 extends into the housing 20 adjacent to the upper head 21 thereof. Such being the case, a lateral annular gap 35 is defined between the cone-shaped baffle 31 and the inner wall of the housing 20. With the arrangement of the cone-shaped baffle 31, the mixed stream from the premixer 10 is introduced radially outward into a region in the housing 20 adjacent to the inner wall thereof via the annular gap 35. By this means, the mixed stream 3 enters the sector tube distributors 41 in a radial outside of the housing 20 more homogeneously.

Advantageously, the gas distributor 30 also serves to further mix butene, air, and steam. Moreover, the arrangement of the cone-shaped baffle 31 in the gas distributor 30 allows the mixed stream 3 to flow through the annular gap 35 with ease, so as to smoothly flow downward along an inner wall of the upper head 21. In this case, a vortex phenomenon and flow energy loss would be prevented in a region around the cone-shaped baffle 31 of the gas distributor 30 and in a region adjacent to the inner wall of the upper head 21 of the housing, thereby lowering the pressure drop in the flow of gases and enabling the mixed stream 3 to be distributed in the sector tube distributors 41 of the housing in a faster and more homogeneous manner. Hence, the utilization ratio of the catalyst bed 42 is improved, while the height of the homogenized space is significantly reduced, whereby the capacity utilization of the reactor is enhanced.

Figure 3:
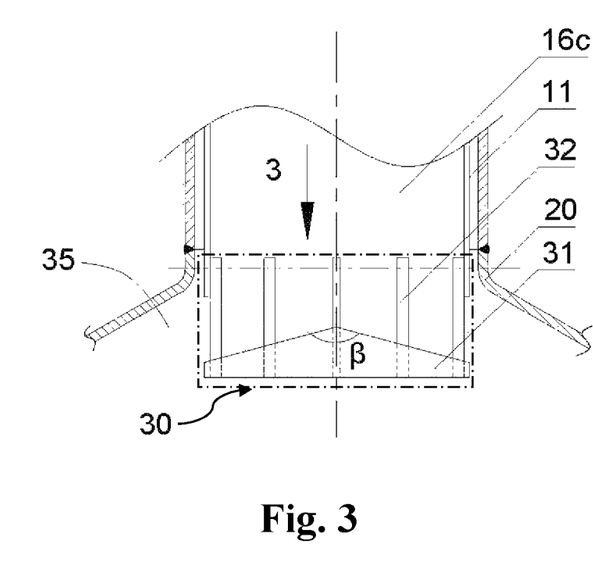
FIG. 3 indicates a gas distributor arranged at a gas inlet of the radially fixed bed reactor in an enlarged view.

FIG. 3 more clearly shows that the cone-shaped baffle 31 of the gas distributor 30 is connected to the open end 13 of the tubular body 11 of the premixer 10 through a plurality of webs 32 circumferentially arranged in a homogeneous manner. Preferably, at least three webs 32 are circumferentially arranged in a homogeneous manner. This structure is simple with reliable connection, and has minimum influences on the flow of gasses.

In one embodiment, a cone angle β of the cone-shaped baffle 31 can be in the range from 90 to 135°, which can ensure homogeneous distribution of the mixed stream 3. Preferably, the lateral annular gap 35 formed between the cone-shaped baffle 31 and the housing 20 is arranged in such a size that the mixed stream 3 flowing therethrough maintains an average speed in the range from 10 to 40 m/s, preferably from 20 to 35 m/s.

In one preferred embodiment, six sector tube distributors 41 are arranged along the inner wall of the housing 20, i.e., each sector tube distributor 41 extends for an angle of 60°. In another embodiment, twenty sector tube distributors 41 are arranged along the inner wall of the housing 20. Each of the sector tube distributors 41 is provided with a plurality of orifices on the top wall and inner side wall thereof. Theses orifices can be homogeneously distributed in whole, or homogeneously distributed in different sections, with the porosity thereof being in the range from 10% to 50%, preferably from 20% to 40%. Thus, it is guaranteed that gases can smoothly flow into the sector tube distributors 41, and then flow out therefrom into the catalyst bed 42.

In one embodiment, the porous wall tube 45 comprises a porous cylinder positioned in a center thereof, a perforated plate abutting against the porous cylinder, and a screen or grill at an outer side thereof (i.e., adjacent to the catalyst bed 42), wherein the screen and the perforated plate are connected to each other via support ribs, or the grill abuts against the perforated plate. The structure of the perforated wall tube is rather simple.

In one embodiment, the porous cylinder and perforated plate of the porous wall tube are both provided with circular holes or elongated circular holes. The open porosity of the porous cylinder is, for example, in the range from 10% to 50%; the open porosity of the perforated plate in the center layer ranges from 20% to 50%, preferably from 20% to 40%; and the voidage of the screen or grill ranges from 10% to 60%, preferably from 20% to 40%.

The arrangement of aforementioned catalyst bed assembly 40 can ensure that the mixed stream is homogeneously distributed in an upper portion and a lower portion of the sector tube distributors 41 before entering the catalyst bed 42 in a homogeneous and smooth manner. Thereby, the catalyst in the catalyst bed 42 can be sufficiently used. Furthermore, the sector tube distributors 41 are of simple structures, large orifice areas, and small pressure drop, which is favorable for gasses to enter the catalyst bed 42 quickly and homogeneously. The reactant gasses flow radially after entering the catalyst bed, ensuring short flowing distance through the catalyst bed 42 and small pressure drop therein, which facilitates improvement of conversion and selectivity.

The use of the radially fixed bed reactor according to the present disclosure will be explained through Examples 1 to 8 and Comparative Example 1 below.

Example 1

The reactor as shown in FIG. 2 is adopted by a 100,000 t/year plant for producing butadiene by oxidative dehydrogenation of butene. Steam and air are introduced into the reactor via the first flow passage 14 at the top end of the premixer 10, and enter the mixing chamber 16c via the perforated distribution plate 15. The feed stock butene is introduced into the distribution chamber 17 from the second flow passage 18 mounted at the side portion of the premixer 10, and enters the mixing chamber 16c via the nozzles 19. In the mixing chamber 16c, butene mixes with steam and air. The mixed stream enters the housing 20 of the reactor 50 via the gas distributor 30 having the cone-shaped baffle 31, and flows into the sector tube distributors 41. The reactant stream then flows into the catalyst bed 42 via the distribution orifices of the sector tube distributors 41, and then into the porous wall tube 45, before running out of the reactor 50 from the discharging outlet 48.

During the reaction, the feed rates of air and the feed stock butene are respectively 36,000 kg/h and 20,000 kg/h. The feed and discharge processes are carried out at a pressure of 0.12 MPa, and respectively at temperatures of 320° C. and 480° C. The second flow passage 18 has a diameter of 400 mm, and the diameter of the first flow passage 14 is 800 mm. The conical tube 16 has a half cone angle α of 15° and a height of 2,000 mm. The perforated distribution plate 15 is in the form of a hemisphere, which is provided with 600 orifices each having a diameter of 32 mm. The housing 20 of the reactor 50 has a diameter of 3,200 mm. The catalyst bed 42 has a height and thickness of respectively 6,000 mm and 650 mm. An iron-based composite oxide catalyst which has a spinel structure is employed, the chemical composition thereof being $Fe_2O_3.MgO.ZnO.P_2O_5.CuO$. 20 sector tube distributors 41 are homogeneously distributed along the inner wall of the housing, and are homogeneously perforated from top to bottom with the porosity thereof being 25%. The porosity of the porous cylinder arranged in the inner side of the porous wall tube 45, and that of the perforated plate in the center are respectively 30% and 50%. The voidage of the screen or grill in the outer side is 23%. The cone-shaped baffle has a cone angle of 135°. The mixed gasses flow through the annular gap 35 at an average speed of 25 m/s.

Tests have shown that the pressure drop of the reactor is 2 kpa; the conversion of butene is 83%; the selectivity is 95.5%; and the catalyst takes a period of 12 months to be regenerated.

Example 2

Example 2 involves a 100,000 t/year plant for producing butadiene by oxidative dehydrogenation of butene. The reactor structures and reaction parameters in Example 2 are substantially the same as those recited in Example 1, except that the half cone angle α of the conical tube 16 is 10° and the height thereof is 2,400 mm; the catalyst has a chemical composition of $Fe_2O_3.MgO.ZnO.P_2O_5.Cr_2O_3$; and the cone angle of the cone-shaped baffle is 120°.

Tests have shown that the pressure drop of the reactor is 2 kpa; the conversion of butene is 82.5%; the selectivity 95%; and the catalyst takes a period of 12 months to be regenerated.

Example 3

Example 3 involves a 100,000 t/year plant for producing butadiene by oxidative dehydrogenation of butene. The reactor structures and reaction parameters in Example 3 are substantially the same as those recited in Example 1, except that the premixer 10 is arranged without a perforated distribution plate, i.e., the second end 14b of the first flow passage 14 is configured to be open, and directly introduces air and steam into the mixing chamber 16c; the catalyst has a chemical composition of $Fe_2O_3.MgO.ZnO.P_2O_5.MnO_2$; and the cone angle of the cone-shaped baffle is 120°.

Tests have shown that the pressure drop of the reactor is 1.8 kpa; the conversion of butene is 83%; the selectivity is 95%; and the catalyst takes a period of 10 months to be regenerated.

Example 4

Example 4 involves a 100,000 t/year plant for producing butadiene by oxidative dehydrogenation of butene. The reactor structures and reaction parameters in Example 4 are substantially the same as those recited in Example 1, except that the housing 20 of the reactor 50 has a diameter of 3,600 mm; the catalyst bed 42 adopts a height of 5,500 mm and a thickness of 600 mm; and the chemical composition of the catalyst is $Fe_2O_3.MgO.ZnO.P_2O_5.CoO$.

Tests have shown that the pressure drop of the reactor is 1.6 kpa; the conversion of butene is 83%; the selectivity is 96%; and the catalyst takes a period of 14 months to be regenerated.

Example 5

Example 5 involves a 100,000 t/year plant for producing butadiene by oxidative dehydrogenation of butene. The reactor structures and reaction parameters in Example 5 are substantially the same as those recited in Example 1, except that the half cone angle α of the conical tube 16 is 10° and the height thereof is 2,400 mm; the catalyst has a chemical composition of $Fe_2O_3.MgO.ZnO.P_2O_5.NiO$; and 23 sector tube distributors 41 are homogeneously distributed along the inner wall of the housing, and are divided into three sections from top to bottom and homogeneously perforated in each section, the perforations in the three sections respectively having a porosity of 22%, 24%, and 26%.

Tests have shown that the pressure drop of the reactor is 1.8 kpa; the conversion of butene is 83.5%; the selectivity is 96%; and the catalyst takes a period of 14 months to be regenerated.

Example 6

Example 6 involves a 100,000 t/year plant for producing butadiene by oxidative dehydrogenation of butene. The reactor structures and reaction parameters in Example 6 are substantially the same as those recited in Example 1, except that the catalyst has a chemical composition of $Fe_2O_3.MgO.ZnO.P_2O_5.Cr_2O_3$; and the porosity of the porous cylinder in the inner wall of the porous wall tube 45 is 40%, and that of the perforated plate in the center is 45%.

Tests have shown that the pressure drop of the reactor is 1.9 kpa; the conversion of butene is 82.5%; the selectivity is 95%; and the catalyst takes a period of 10 months to be regenerated.

Example 7

Example 7 involves a 100,000 t/year plant for producing butadiene by oxidative dehydrogenation of butene. The reactor structures and reaction parameters in Example 7 are substantially the same as those recited in Example 1, except that the catalyst has a chemical composition of $Fe_2O_3.MgO.ZnO.P_2O_5.Cr_2O_3$; and the mixed gasses flow through the annular gap 35 at an average speed of 35 m/s.

Tests have shown that the pressure drop of the reactor is 2.5 kpa; the conversion of butene is 82%; the selectivity is 94%; and the catalyst takes a period of 9 months to be regenerated.

Example 8

Example 8 involves a 100,000 t/year plant for producing butadiene by oxidative dehydrogenation of butene. The reactor structures and reaction parameters in Example 8 are substantially the same as those recited in Example 1, except that the feed rates of air and the feed stock butene are respectively 34,000 kg/h and 19,000 kg/h; the feed and discharge processes are carried out at a pressure of 0.15 MPa, and respectively at temperatures of 360° C. and 510° C.; the second flow passage 18 has a diameter of 450 mm, and the diameter of the first flow passage 14 is 900 mm; the conical tube 16 has a half cone angle α of 12°; the perforated distribution plate 15 has a diameter of 38 mm; the catalyst adopt an iron-based composite oxide having a spinel structure, the chemical composition thereof being $Fe_2O_3 \cdot MgO \cdot ZnO \cdot P_2O_5 \cdot CuO$; twenty sector tube distributors 41 are homogeneously distributed along the inner wall of the housing, and are homogeneously perforated from top to bottom with the porosity thereof being 25%; and the cone-shaped baffle has a cone angle of 120°.

Tests have shown that the pressure drop of the reactor is 2 kpa; the conversion of butene is 84%; the selectivity is 94%; and the catalyst takes a period of 10 months to be regenerated.

Comparative Example 1

Comparative Example 1 involves a 100,000 t/year plant for producing butadiene by oxidative dehydrogenation of butene. The plant adopts an axially fixed bed reactor, wherein four reactors are operated in parallel, each having a diameter of 3,200 mm, and a catalyst bed thickness of 600 mm. The feed rates of air and the feed stock butene are respectively 36,000 kg/h and 20,000 kg/h. The feed and discharge processes are carried out at a pressure of 0.12 MPa, and respectively at temperatures of 320° C. and 480° C. The axially fixed bed reactor is not provided with the premixer as shown in FIG. 1, or the gas distributor as shown in FIG. 2.

Tests have shown that the pressure drop of the reactor is 20 kpa; the conversion of butene is 75%; the selectivity is 88%; and the catalyst takes a period of 3 months to be regenerated.

The results of Examples 1 to 8, and Comparative Example 1 are indicated in Table 1 below.

TABLE 1

|  | Pressure drop (kPa) | Conversion of butene (%) | Selectivity of butadiene (%) | Regeneration period of catalyst (month) |
| --- | --- | --- | --- | --- |
| Example 1 | 2 | 83 | 95.5 | 12 |
| Example 2 | 2 | 82.5 | 95 | 12 |
| Example 3 | 1.8 | 83 | 95 | 10 |
| Example 4 | 1.6 | 83 | 96 | 14 |
| Example 5 | 1.8 | 83.5 | 96 | 14 |
| Example 6 | 1.9 | 82.5 | 95 | 10 |
| Example 7 | 2.5 | 82 | 94 | 9 |
| Example 8 | 2 | 84 | 94 | 10 |
| Comparative Example 1 | 20 | 75 | 88 | 3 |

As shown in Table 1, the unique premixer and gas distributor adopted by the radially fixed bed reactor according to the present disclosure ensures fast and homogeneous mixing of the feed stocks of butene, and steam and air, which allows gas flow that enters the reactor to be homogeneously distributed. Under the same production scale, the pressure drop in the radially fixed bed reactor is reduced by 50% to 90% compared with that of the axially fixed bed reactor having the same diameter, the utilization ratio of catalyst thereof improved by 30%, the conversion improved by 5% to 10%, and the selectivity improved by 3% to 10%. Hence, the radially fixed bed reactor according to the present disclosure is capable of obtaining excellent technical effects.

The present disclosure further relates to a system used in the preparation of butadiene by oxidative dehydrogenation of butene. This system is to be described in detail with reference to FIGS. 4 to 6.

Figure 4:
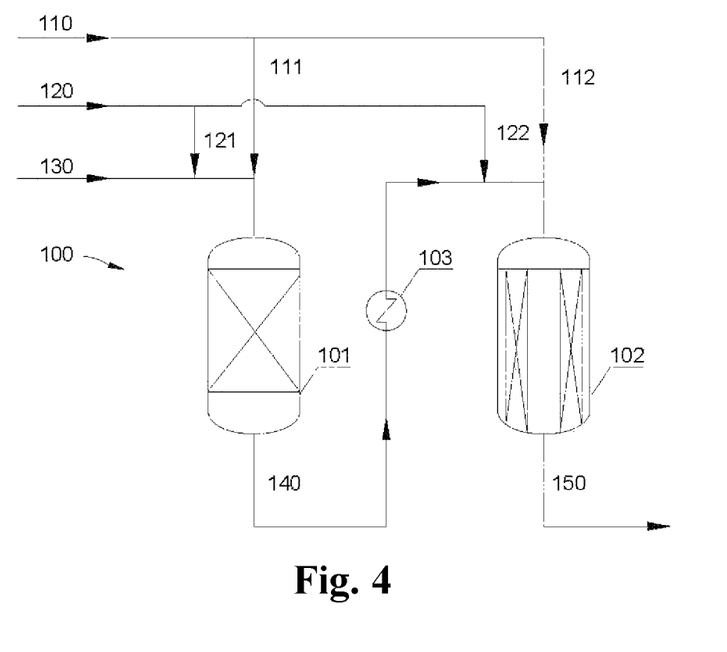
FIGS. 4 to 6 schematically show three examples of a reaction system of oxidative dehydrogenation of butene according to the present disclosure, respectively.

FIG. 4 shows a reaction system 100 for oxidative dehydrogenation of butene according to one embodiment of the present disclosure. As indicated in the Figure, the system 100 comprises an upstream, axially fixed bed reactor 101, and a downstream, radially fixed bed reactor 102 in series connection with each other. The upstream reactor can also be referred to as the first stage reactor, and the downstream reactor as the second stage reactor. The axially fixed bed reactor 101 employs a conventional structure, with the specific design thereof being well known in the art, and therefore will not be explained here in detail. The radially fixed bed reactor 102 of the system 100 adopts the structure as indicated in FIG. 2. Preferably, a heat exchanger 103 can be disposed between the axially fixed bed reactor 101 and the radially fixed bed reactor 102.

According to the present disclosure, a butene feed stream 110 is divided into a stream 111 and a stream 112, which are respectively fed into the axially fixed bed reactor 101, and the radially fixed bed reactor 102. The feed stock butene can comprise at least one from the group consisting of 1-butene, cis-2-butene, and trans-2-butene. An oxygen-containing stream 120 is also divided into two streams, i.e., a stream 121 and a stream 122, which are respectively fed into the axially fixed bed reactor 101, and the radially fixed bed reactor 102. The oxygen-containing stream can, for example, be air or pure oxygen, or a mixture of air and oxygen. Steam 130 is fed into the axially fixed bed reactor 101.

In this way, the butene stream 111, the oxygen-containing stream 121, and steam 130 are fed into the axially fixed bed reactor 101 together. The ratio of butene to the oxygen-containing gas to steam that enter the axially fixed bed reactor 101 can, for example, be in the range from 1:(0.4-1.5):(2-20), preferably from 1:(0.45-0.9):(6-16). These gasses react with one another in the axially fixed bed reactor 101, and produce a first output stream 140. The butene in the axially fixed bed reactor 101 can have an hourly space velocity ranging from 200 to 450 $h^{-1}$.

The first output stream 140, after passing through the heat exchanger 103, is fed into the radially fixed bed reactor 102 together with the butene stream 112, and the oxygen-containing stream 122. The ratio of butene to the oxygen-containing gas to steam that enter the radially fixed bed reactor 102 can, for example, range from 1:(0.4-1.5):(2-20), preferably from 1:(0.45-0.9):(6-16). These gasses react with one another in the radially fixed bed reactor 102, and produce a second output stream 150. The butene in the radially fixed bed reactor 102 has an hourly space velocity ranging from 200 to 450 $h^{-1}$.

The second output stream 150 enters a downstream separation stage (not shown) for recovering butadiene. Since the separation stage is well known by one skilled in the art, it will not be described here in detail. One skilled in the art also knows well about the process of recovering butadiene, such as condensation, washing, and oil absorption of the reactant streams, and extractive distillation of butadiene.

In both the axially fixed bed reactor 101 and the radially fixed bed reactor 102, the reaction temperature ranges from 300 to 600° C., preferably from 310 to 480° C., and more preferably from 310 to 380° C.; and the reaction pressure ranges from 0.0 to 2.0 MPaG, preferably from 0.05 to 0.5 MPaG. The ratio of butene to oxygen-containing gas to steam at each reactor inlet is preferably in the range from 1:(0.5-0.8):(6-12), more preferably from 1:(0.5-0.7):(6-10), and still more preferably from 1:(0.5-0.6):(8-10).

According to the present disclosure, the reactor system of oxidative dehydrogenation of butene comprises at least two heat insulation fixed bed reactors. In the embodiment as shown in FIG. 4, the reaction system 100 includes the axially fixed bed reactor 101, and the radially fixed bed reactor 102 in series connection with each other. The axially fixed bed reactor is of simple structure, convenient operations, and small investment. However, pressure drop control in an axially fixed bed reactor is difficult for pressure-sensitive reactions such as oxidative dehydrogenation of butene, and massive scale practice therein is therefore unrealizable. On the other hand, a radially fixed bed reactor has a favorably smaller pressure drop for corresponding reactions, and the same scale apparatus thereof covers a smaller floor area than an axially fixed bed reactor does. Nevertheless, a radially fixed bed reactor is of complex structures, and is highly demanding in design of homogeneous distribution of gasses and apparatus investment. Therefore, the reaction system according to the present disclosure which connects the axially and radially fixed bed reactors in series can largely develop the respective advantages of both of the two reactors. Thereby, the amounts of butene respectively entering these two reactors can be adjusted with flexibility. Furthermore, the reaction pressure drop is decreased, and the conversion of butene is increased without large investment in apparatuses. Meanwhile, since steam enters the upstream fixed bed reactors completely (the radially fixed bed reactor 101 in the embodiment as indicated in FIG. 4), a high ratio of water to butene is obtainable in each reactor with a comparatively low total ratio of water to butene in the whole apparatus, which facilitates control of heat insulation rise, and prevention of catalyst coking. In addition, decrease in the total ratio of water to butene means effective decrease in energy consumption.

Figure 5:
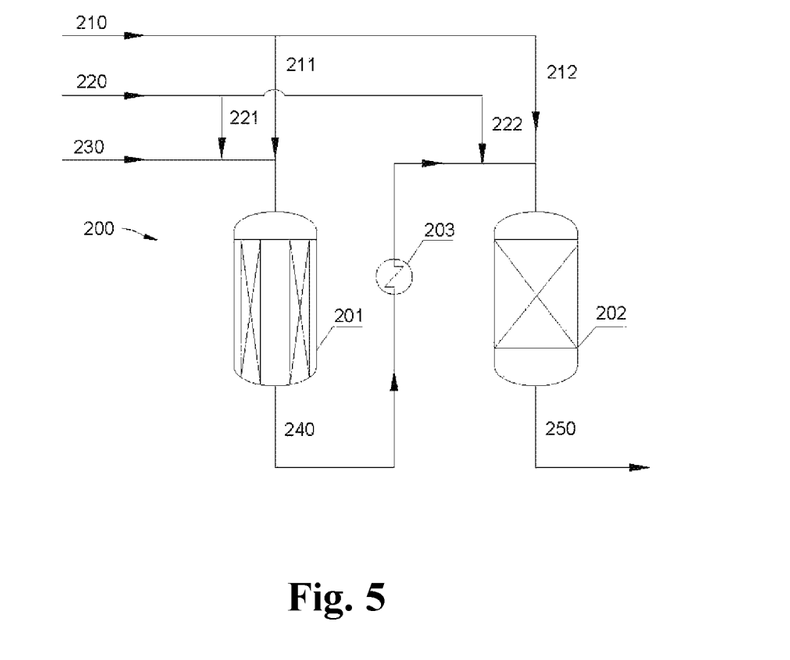

FIG. 5 shows a reaction system 200 for oxidative dehydrogenation of butene according to another embodiment of the present disclosure. As illustrated in the Figure, the reaction system 200 includes an upstream, radially fixed bed reactor 201, and a downstream, axially fixed bed reactor 202 in series connection with each other. The axially fixed bed reactor 202 employs a conventional structure, and the radially fixed bed reactor 201 adopts the structure as indicated in FIG. 2. Preferably, a heat exchanger 203 can be disposed between the radially fixed bed reactor 201 and the axially fixed bed reactor 202.

According to the present disclosure, a butene feed stream 210 is divided into two streams, i.e., a stream 211 and a stream 212, which are respectively fed into the radially fixed bed reactor 201, and the axially fixed bed reactor 202. An oxygen-containing stream 220 is also divided into two streams, i.e., a stream 221 and a stream 222, which are respectively fed into the radially fixed bed reactor 201, and the axially fixed bed reactor 202. Steam 230 is fed into the radially fixed bed reactor 201.

In this way, the butene stream 211, the oxygen-containing stream 221, and steam 230 are fed into the radially fixed bed reactor 201 together. These gasses react with one another in the radially fixed bed reactor 201, and produce a first output stream 240. The first output stream 240, after passing through the heat exchanger 203, is fed into the axially fixed bed reactor 202 together with the butene stream 212, and the oxygen-containing stream 222. These gasses react with one another in the axially fixed bed reactor 202, and produce a second output stream 250. The second output stream 250 enters a downstream separation apparatus (not shown) for recovering butadiene.

Figure 6:
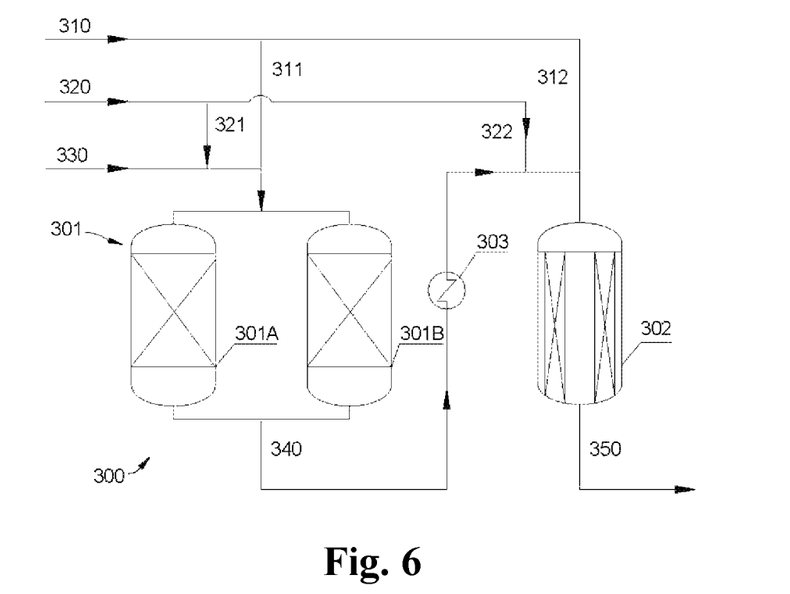

FIG. 6 shows a reaction system 300 for oxidative dehydrogenation of butene according to another example of the present disclosure. As illustrated in the Figure, the reaction system 300 includes an upstream, axially fixed bed reactor unit 301, and a downstream, radially fixed bed reactor 302 in series connection with each other. The axially fixed bed reactor unit 301 comprises two axially fixed bed reactors 301A and 301B which employ a conventional structure and are in parallel connection with each other. The radially fixed bed reactor 302 adopts the structure as indicated in FIG. 2. Preferably, a heat exchanger 303 can be disposed between the axially fixed bed reactor unit 301 and the radially fixed bed reactor 302.

According to the present disclosure, a butene feed stream 310 is divided into two streams, i.e., a stream 311 and a stream 312, which are respectively fed into the axially fixed bed reactor unit 301, and the axially fixed bed reactor 302. An oxygen-containing stream 320 is also divided into two streams, i.e., a stream 321 and a stream 322, which are respectively fed into the axially fixed bed reactor unit 301, and the radially fixed bed reactor 302. Steam 330 is fed into the radially fixed bed reactor 302.

In this way, the butene stream 311, the oxygen-containing stream 321, and steam 330 are together fed into 301A and 301 B of the axially fixed bed reactor unit 301. These gasses react with one another in the axially fixed bed reactors 301A and 301B, and produce a first output stream 340. The first output stream 340, after passing through the heat exchanger 303, is fed into the radially fixed bed reactor 302 together with the butene stream 312, and the oxygen-containing stream 322. These gasses react with one another in the radially fixed bed reactor 302, and produce a second output stream 350. The second output stream 350 enters a downstream separation apparatus (not shown) for recovering butadiene.

The use of the reaction system for oxidative dehydrogenation of butene according to the present disclosure will be explained through Examples 9 to 14 and Comparative Example 2 below.

Example 9

Example 9 involves a 100,000 t/year plant for producing butadiene by oxidative dehydrogenation of butene. Said plant adopts the reaction system as shown in FIG. 4. The axially fixed bed reactor 101 has a diameter of 4.5 m; the catalyst bed thereof is 600 mm high; and the hourly space velocity of butene is 400 $h^{-1}$. The radially fixed bed reactor 102 has a diameter of 3.2 m; the catalyst bed thereof is 600 mm thick, 6,000 mm high, and has a height to diameter ratio of 10; and the hourly space velocity of butene is 300 $h^{-1}$.

The feed rates of the feed stock butene, air, and steam are respectively 20,000 kg/h and 36,000 kg/h, and 66,000 kg/h. The feed stock butene is divided into two parts. The butene stream 111, at a flow rate of 7,000 kg/h, is mixed with oxygen and steam, with the molar ratio of butene to oxygen to steam as 1:0.55:15. Afterwards, the resulting mixed stream enters the axially fixed bed reactor 101 at a temperature of 320° C. and a pressure of 0.15 MPaG. The first output stream 140 with a temperature of 480° C. at the material outlet, after passing through the heat exchanger 103, is mixed with the butene stream 112, and air stream 122, before subsequently entering the radially fixed bed 102. The butene stream 112 flows at a rate of 13,000 kg/h, and the butene, oxygen, and steam enter the radially fixed bed reactor 102 with a molar ratio thereof being 1:0.65:16. The reaction temperature in the radially fixed bed reactor is 330° C.; the pressure thereof is 0.1 MPaG; and the second output stream 150 has a temperature of 510° C.

The reaction system 100 has an annual butadiene production capacity of 100,000 tons, wherein 35% of the total feed stock butene is processed in the axially fixed bed reactor 101, and the rest 65% is processed in the radially fixed bed reactor 102. The conversion of butene is 80%. The energy consumption of the plant is 1,200 kg of standard oil per ton of butadiene. And a total amount of RMB 20 million is invested in the reactors.

Example 10

Example 10 involves a 100,000 t/year plant for producing butadiene by oxidative dehydrogenation of butene. Said plant adopts the reaction system as shown in FIG. 5. The radially fixed bed reactor 201 has a diameter of 3.5 m; the catalyst bed thereof is 600 mm thick, 6,000 mm high, and has a height to diameter ratio of 10; and the hourly space velocity of butene is 350 h$^{-1}$. The axially fixed bed reactor 202 has a diameter of 5 m; the catalyst bed thereof is 550 mm high; and the hourly space velocity of butene is 400 h$^{-1}$. The feed rates of the feed stock butene, air, and steam are respectively 20,000 kg/h and 36,000 kg/h, and 66,000 kg/h. The feed stock butene is divided into two parts. The butene stream 211, at a flow rate of 14,000 kg/h is mixed with oxygen and steam, with the molar ratio of butene to oxygen to steam as 1:0.6:10. Afterwards, the resulting mixed stream enters the radially fixed bed reactor 201 at a temperature of 320° C. and a pressure of 0.15 MPaG. The first output stream 240 with a temperature of 500° C., after passing through the heat exchanger 203, is mixed with the butene stream 212, and air stream 222, before subsequently entering the axially fixed bed 202. The butene stream 212 flows at a rate of 6,000 kg/h, and the butene, oxygen, and steam enter the axially fixed bed reactor 202 with a molar ratio thereof being 1:0.6:16. The reaction temperature in the axially fixed bed reactor is 330° C. and the pressure thereof is 0.12 MPaG. The second output stream 250 has a temperature of 500° C.

The reaction system 200 has an annual butadiene production capacity of 100,000 tons, wherein 70% of the total feed stock butene is processed in the radially fixed bed reactor 201, and the rest 30% is processed in the axially fixed bed reactor 202. The conversion of butene is 81%. The energy consumption of the plant is 1,200 kg of standard oil per ton of butadiene. And a total amount of RMB 22 million is invested in the reactors.

Example 11

Example 11 involves a 100,000 t/year plant for producing butadiene by oxidative dehydrogenation of butene. Said plant adopts the reaction system as shown in FIG. 6. Two axially fixed bed reactors 301A and 301B in parallel are arranged in the upstream, wherein each reactor has a diameter of 4 m; the catalyst bed thereof is 600 mm high; and the hourly space velocity of butene is 400 h$^{-1}$. The radially fixed bed reactor 302 has a diameter of 3 m; the catalyst bed thereof is 600 mm thick, 6,000 mm high, and has a height to diameter ratio of 10; and the hourly space velocity of butene is 300 h$^{-1}$. The feed rates of the feed stock butene, air, and steam are respectively 20,000 kg/h and 35,000 kg/h, and 64,000 kg/h. The feed stock butene is divided into two parts, wherein the butene stream 311 flows at a rate of 12,000 kg/h, and the feed rates of butene in the axially fixed bed reactors 301A and 301B are both 6,000 kg/h. The molar ratio of butene to oxygen to steam is 1:0.55:15. The temperature in the axially fixed bed reactor is 320° C., and the pressure thereof is 0.14 MPaG. The first output stream 340 with a temperature of 480° C., after passing through the heat exchanger 303, is mixed with the butene stream 312, and air stream 322, before subsequently entering the radially fixed bed 302. The butene stream 312 flows at a rate of 8,000 kg/h, and the butene, oxygen, and steam enter the radially fixed bed reactor 302 with a molar ratio thereof being 1:0.65:12. The reaction temperature in the radially fixed bed reactor 302 is 330° C. and the pressure thereof is 0.1 MPaG. The second output stream 350 has a temperature of 500° C.

The reaction system has an annular butadiene production capacity of 106,000 tons, wherein 60% of the total feed stock butene is processed in the axially fixed bed reactor 301, and the rest 40% is processed in the radially fixed bed reactor 302. The conversion of butene is 84%. The energy consumption of the plant is 1,150 kg of standard oil per ton of butadiene. And a total amount of RMB 20 million is invested in the reactors.

Example 12

Example 12 involves a 100,000 t/year plant for producing butadiene by oxidative dehydrogenation of butene. Said plant is substantially the same as the plant in Example 9, except that the molar ratio of butene to oxygen to steam in the axially fixed bed reactor 101 is 1:0.55:8, with the reaction pressure thereof being 0.20 MPaG; and the reaction pressure in the radially fixed bed reactor 102 is 0.15 MPaG.

The reaction system has an annual butadiene production capacity of 95,000 tons, wherein 35% of the total feed stock butene is processed in the axially fixed bed reactor 101, and the rest 65% is processed in the radially fixed bed reactor 102. The conversion of butene is 78%. The energy consumption of the plant is 1,300 kg of standard oil per ton of butadiene. And a total amount of RMB 20 million is invested in the reactors.

Example 13

Example 13 involves a 100,000 t/year plant for producing butadiene by oxidative dehydrogenation of butene. Said plant is substantially the same as the plant in Example 9, except that the diameter of the axially fixed bed reactor 101 is 4.0 m; the radially fixed bed reactor 102 has a diameter of 2.8 m; the oxygen flows at a rate of 7,500 kg/h; and the molar ratio of butene to oxygen to steam in the axially fixed bed reactor 101 is 1:0.55:6.

The reaction system has an annual butadiene production capacity of 102,000 tons, wherein 35% of the total feed stock of butene is processed in the axially fixed bed reactor 101, and the rest 65% is processed in the radially fixed bed reactor 102. The conversion of butene is 83%. The energy consumption of the plant is 1,000 kg of standard oil per ton of butadiene. And a total amount of RMB 18 million is invested in the reactors.

Example 14

Example 14 involves a 100,000 t/year plant for producing butadiene by oxidative dehydrogenation of butene. Said plant is substantially the same as the plant in Example 11, except that in the axially fixed bed reactors 301A and 301B, each of the catalyst beds is 700 mm high, and the hourly space velocity of butene thereof is 300 $h^{-1}$; in the radially fixed bed reactor 302, the catalyst bed has a thickness of 650 mm, a height of 6,500 mm, and the hourly space velocity of butene thereof is 400 $h^{-1}$; the molar ratio of butene to oxygen to steam in the axially fixed bed reactors 301A and 301B is 1:0.50:10, and the reaction pressure thereof is 0.15 MPaG; the first output stream 340 has a temperature of 490° C.; and butene, oxygen, and steam enter the radially fixed bed reactor 302 with a molar ratio of 1:0.65:10.

The reaction system has an annual butadiene production capacity of 100,000 tons, wherein 55% of the total feed stock of butene is processed in the axially fixed bed reactor unit 301, and the rest 45% is processed in the radially fixed bed reactor 302. The conversion of butene is 85%. The energy consumption of the plant is 1,150 kg of standard oil per ton of butadiene. And a total amount of RMB 20 million is invested in the reactors.

Comparative Example 2

Figure 7:
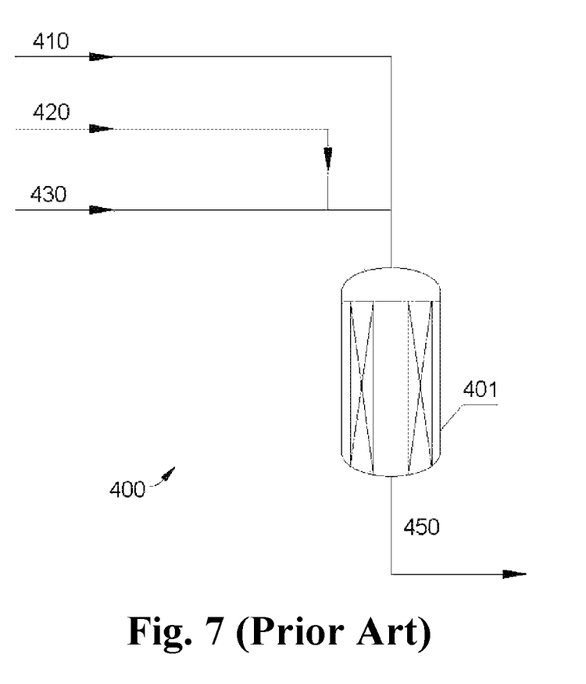
FIG. 7 schematically shows the reaction system of oxidative dehydrogenation of butene according to a comparative example.

Comparative Example 2 involves a 100,000 t/year plant for producing butadiene by oxidative dehydrogenation of butene. Said plant adopts the reaction system as shown in FIG. 7. A conventionally used, single, axially fixed and heat insulated bed reactor 401 is adopted. Feed stock butene 410, air 420, and steam 430 respectively flow at a rate of 22,700 kg/h; 34,000 kg/h, and 160,500 kg/h. The molar ratio of butene to oxygen to steam is 1:0.6:22. The reaction temperature is 330° C., and the reaction pressure 0.12 MPaG. An output gas 450 has a temperature of 520° C.

The consumption of steam in the reaction stages is 131,330 kg/h, the energy consumption of the plant is 1,600 kg of standard oil per ton of butadiene. And the conversion of butene is 65%.

The statistics obtained in the above Examples and Comparative Example indicate that with the reaction system according to the present disclosure, the conversion of butene can be improved by 10% to 20%; the investment amount at the same scale as in a conventional reaction system can be reduced by 10% to 30%; and the plant can save more than 20% of energy. Therefore, excellent technical effects are obtainable through the reaction system according to the present disclosure.

Although the present disclosure has been discussed with reference to preferable embodiments, it extends beyond the specifically disclosed embodiments to other alternative embodiments and/or use of the disclosure and obvious modifications and equivalents thereof. Particularly, as long as there are no structural conflicts, the technical features disclosed in each and every embodiment of the present disclosure can be combined with one another in any way. The scope of the present disclosure herein disclosed should not be limited by the particular disclosed embodiments as described above, but encompasses any and all technical solutions following within the scope of the following claims.

The invention claimed is:

1. A system for preparing butadiene by oxidative dehydrogenation of butene, comprising:
   a first stage reactor and a second stage reactor connected to each other, wherein the first stage reactor is an axially fixed bed reactor and the second stage reactor is a radially fixed bed reactor, or the first stage reactor is the radially fixed bed reactor and the second stage reactor is the axially fixed bed reactor,
   wherein the radially fixed bed reactor comprises:
   a premixer for mixing at least a first gas and a second gas, wherein the premixer comprises:
   a tubular body having a closed end and an open end;
   a first flow passage for receiving the first gas, the first flow passage axially and sealably extending through the closed end into the tubular body;
   a conical tube arranged in the tubular body, wherein a small end of the conical tube communicates with the first flow passage, and a large end of the conical tube extends toward the open end with an edge thereof affixed to an inner wall of the tubular body, thereby defining a sealed distribution chamber between the tubular body and the conical tube; and
   a second flow passage arranged on a side portion of the tubular body for delivering the second gas into the distribution chamber;
   a cylindrical housing with a top end communicating with the open end of the tubular body of the premixer;
   a catalyst bed assembly disposed in the housing, wherein the catalyst bed assembly comprises a plurality of sector tube distributors disposed on an inner wall of the housing, a porous wall tube disposed in the center of the housing and extending outside from the housing, and a catalyst bed disposed between the plurality of sector tube distributors and the porous wall tube,
   wherein a sealing member is arranged at an upper end of the catalyst bed, which allows a gas stream from the premixer to enter the plurality of sector tube distributors and to discharge from the housing after passing through the catalyst bed and the porous wall tube; and
   a gas distributor attached to the open end of the tubular body of the premixer and extends into the housing, a lower end of the gas distributor being provided with a cone-shaped, non-porous baffle tapered toward the tubular body, whereby guiding all of a gas from the premixer to enter the housing via a lateral annular gap formed between the cone-shaped baffle and the housing.

2. The system according to claim 1, wherein, in the radially fixed bed reactor, the gas distributor further comprises a plurality of webs circumferentially arranged in a homogeneous manner for connecting the cone-shaped baffle to the open end of the tubular body of the premixer.

3. The system according to claim 1, wherein, in the radially fixed bed reactor, a cone angle of the cone-shaped baffle ranges from 90° to 135°.

4. The system according to claim 1, wherein, in the radially fixed bed reactor, the lateral annular gap is arranged in such a size that the mixed gasses flowing therethrough maintains an average speed from 10 to 40 m/s.

5. The system according to claim 1, wherein, in the radially fixed bed reactor, at least six sector tube distributors are circumferentially arranged along the inner wall of the housing, wherein each sector tube is perforated with a plurality of distribution orifices.

6. The system according to claim 5, wherein a porosity of the distribution orifices ranges from 10% to 50%.

7. The system according to claim 1, wherein, in the radially fixed bed reactor, the porous wall tube comprises a porous cylinder positioned in a center thereof, a perforated plate abutting against the porous cylinder, and a screen or grill disposed about the porous wall tube, wherein the screen and the perforated plate are connected to each other via support ribs, or the grill abuts against the perforated plate.

8. The system according to claim 1, wherein the axially fixed bed reactor comprises at least two axially fixed bed reactors connected to each other in parallel.

9. The system according to claim 1, wherein, in the radially fixed bed reactor, the first flow passage is tubular in shape and extends into the conical tube by sealably passing through the small end thereof.

10. The system according to claim 9, wherein, in the radially fixed bed reactor, an end of the first flow passage extending into the conical tube comprises a perforated distribution plate, and is in a shape of a hemisphere, a cone, or a plate, the perforations therein having a diameter from 5 mm to 100 mm.

11. The system according to claim 1, wherein, in the radially fixed bed reactor, a half cone angle of the conical tube is from 5° to 20°.

12. The system according to claim 1, wherein the radially fixed bed reactor comprises a plurality of nozzles disposed in a side portion of the conical tube adjacent to the small end thereof for introducing the second gas into the conical tube.

13. The system according to claim 12, wherein the plurality of nozzles are arranged in groups of imaginary concentric circles along an axial direction along the conical tube.

14. The system according to claim 13, wherein the nozzles in every two adjacent groups are staggered from each other in a circumferential direction.

15. The system according to claim 14, wherein the first gas is a mixture of steam and an oxygen-containing gas, and the second gas is butene.

16. The system according to claim 10, wherein the perforations have a diameter ranging from 20 mm to 60 mm.

17. The system according to claim 11, wherein the half cone angle of the conical tube ranges from 8° to 16°.

18. The system according to claim 12, wherein each of the plurality of the nozzles is configured as a guiding cone.

19. The system according to claim 3, wherein the cone angle of the cone-shaped baffle ranges from 120° to 135°.

20. The system according to claim 4, wherein the average speed of the mixed gasses ranges from 20 to 35 m/s.

21. The system according to claim 6, wherein the porosity of the distribution orifices ranges from 20% to 40%.

22. A process for preparing butadiene by a system of claim 1, comprising:
 a) feeding steam into the first stage reactor, and feeding a butene-containing gas and an oxygen-containing gas into both the first stage reactor and the second stage reactor, wherein the molar ratio of butene to oxygen to steam fed into the first stage reactor is 1:(0.4-1.5):(2-20);
 b) mixing materials output from the first stage reactor with the butene-containing gas and oxygen-containing gas before entering the second stage reactor, wherein a molar ratio of butene to oxygen to steam fed into the second stage reactor is 1:(0.4-1.5):(2-20); and
 c) separating materials output from the second stage reactor in a downstream separation stage to obtain butadiene;
  wherein the reaction temperatures in the first and second stage reactors are from 300° C. to 600° C., and the reaction pressures thereof are from 0.0 to 2.0 MPaG.

23. The process according to claim 22, wherein said butene-containing gas comprises at least one selected from the group consisting of 1-butene, cis-2-butene, and trans-2-butene.

24. The process according to claim 22, wherein the molar ratio of butene to oxygen to steam entering each stage is 1:(0.45-0.9):(6-16), wherein the gaseous hourly space velocity of butene entering each stage ranges from 200 to 450 h$^{-1}$; and wherein the reaction temperature in each stage ranges from 310° C. to 480° C., and the reaction pressure in each stage ranges from 0.05 to 0.5 MPaG.

* * * * *